United States Patent [19]

Hao

[11] Patent Number: 6,051,159
[45] Date of Patent: Apr. 18, 2000

[54] SOFT ICE

[76] Inventor: Jie Hao, 10, Bei Yuan St., New City Dis., Hohhot, Inner Mongonia, 001010, China

[21] Appl. No.: 09/033,085

[22] Filed: Mar. 2, 1998

Related U.S. Application Data

[63] Continuation-in-part of application No. 08/670,597, Jun. 26, 1996, Pat. No. 5,723,063

[60] Provisional application No. 60/008,902, Dec. 19, 1995.

[51] Int. Cl.⁷ .............................. C09K 3/18; B01J 13/00; C08J 3/05; C08K 5/053

[52] U.S. Cl. .............................. 252/70; 62/459; 206/811; 252/311; 252/315.1; 383/901; 524/388; 524/916; 526/932

[58] Field of Search .......................... 252/70, 311, 315.1; 62/459; 206/811; 383/901; 524/388, 916; 526/932

[56] References Cited

U.S. PATENT DOCUMENTS

| | | | |
|---|---|---|---|
| 2,516,166 | 7/1950 | Wiczer | 252/70 |
| 2,595,328 | 5/1952 | Bowen | 252/70 |
| 3,463,161 | 8/1969 | Andrassy | 252/70 |
| 3,960,584 | 6/1976 | Savage | 106/174.1 |
| 4,240,436 | 12/1980 | Singleton | 607/108 |
| 4,254,008 | 3/1981 | Krsek | 524/388 |
| 4,537,695 | 8/1985 | Hawe et al. | 252/70 |
| 4,619,778 | 10/1986 | Chalk et al. | 252/70 |
| 4,951,666 | 8/1990 | Inman et al. | 607/114 |
| 5,109,841 | 5/1992 | Hubbard et al. | 128/897 |
| 5,133,348 | 7/1992 | Mayn | 607/108 |
| 5,723,063 | 3/1998 | Jie | 252/70 |

OTHER PUBLICATIONS

Derwent Abstract No. 1997–259697, abstract of Chinese patent specification No. 1101066 (Apr. 1995).

*Primary Examiner*—Anthony Green
*Attorney, Agent, or Firm*—Glenna Hendricks

[57] ABSTRACT

This invention relates to a preferred composition for use in preparation of flexible cold packs which are useful for medicinal, research and other uses where cooling to low temperatures is required.

10 Claims, 2 Drawing Sheets

SOFT ICE

This application is a continuation-in-part of U.S. patent application Ser. No. 08/670,597, filed Jun. 26, 1996, which issued on Mar. 8, 1998 as U.S. Pat. No. 5,723,063, which took priority from Provisional Patent Application No. 60/008,902 filed Dec. 19, 1995.

FIELD OF THE INVENTION

This invention relates to a preferred composition for use in preparation of flexible cold packs which are useful for medicinal, research and other uses where cooling to low temperatures is required.

BACKGROUND OF THE INVENTION

There is presently need for cold packs that will be flexible whilst maintaining very low temperatures. Several approaches have been tried to provide packs that will meet the needs for both flexibility and sufficiently low temperatures for long periods of time for medical, industrial, research and recreational applications.

U.S. Pat. No. 4,240,436 to Singleton, which is incorporated herein in its entirety by reference, discloses a disposable perineal ice pack particularly adapted for treatment of swelling and other disfunction in the rectal-vaginal pelvis region. The pack is composed of a flexible hollow synthetic material having a cold temperature storage medium such as water or other liquid freezable material that freezes at between 0° F. and 32° F. The pack is specialized and expensive to produce and use. An alcohol/water slurry is suggested for use to fill the pack disclosed therein.

U.S. Pat. No. 4, 951,666 to Inman, et al., which is incorporated herein in its entirety by reference, teaches a thermal pack for use in treating a localized injury. The pack includes a porous outer bag and a non-porous inner bag which is foldable between a retracted position within the outer bag and an extended position in which the inner bag protrudes from the outer bag for filling. A flap extends from the open mouth of the inner bag to create a funnel for filling the inner bag. Flexibility of the bag depends on the shape of the bag. The bag is particularly adapted for use on the extremities. There is no teaching of how to use the bag using a flexible filling material that is flexible below the freezing temperature of water.

U.S. Pat. No. 5,109,841 to Hubbard, et al., which is incorporated herein in its entirety by reference, discloses an ice pack for use around the face. The pack comprises a waterproof envelope having a sealable open end and a closed end. A strap is attached at one end of the waterproof envelope and has a centrally disposed longitudinal slit. No method of rendering the pack flexible at very low temperatures by use of flexible ice is disclosed therein.

U.S. Pat. No. 5,133,348 to Mayn, which is incorporated herein in its entirety by reference, discloses a pack which may be filled with hot water or cold water or ice. The pack has four radially extending portions attached thereto and integral therewith. The pack is particularly useful for application to a curved contour of the body.

The prior application, which is a parent of the instant application, discloses a wider variation in ranges for use of the various ingredients. The instant application claims a somewhat narrower range for ingredients.

None of the packs claimed teach use of a cold filling which is flexible at temperatures below the freezing point of water. None of the reference packs disclosed is useful without refilling.

DETAILED DESCRIPTION OF THE INVENTION

Figure 1:
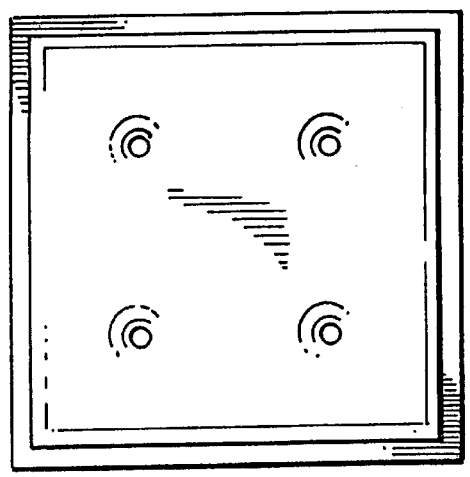
FIG. 1 shows a pack of the invention.

The instant invention provides a filing material (referred to herein as "soft ice") for use in making cold packs which are appropriate for laboratory, medical, industrial or home uses. The soft ice compositions are inexpensive and do not change state under high temperatures. Because the compositions of the invention remain flexible at low temperatures to −7° C., the packs of the invention may be made in several varying shapes and provide cushioning effect which is particularly valuable for making packs to be used to transfer easily broken materials such as vials of biological materials.

The compositions of the invention contain the following materials:

70% to 80% water

5% to 10% salts

12–15% glycerine

3–5% polyacrylamide

Preferred salts include chlorides, sulfates and sulfites. The formulations are prepared by dissolving the salts in the water, then adding the glycerine and polyacrylamide to the water and mixing until a colloidal composition is obtained.

EXAMPLE 1

To 500 grams of water was added 55 grams sodium sulfate with mixing until the sulfate had been dissolved. 130 grams glycerine and 30 grams polyacrylamide were then added to the water/salt solution and the whole was mixed until a colloidal composition was obtained, after which water was added to provide a total weight of 1000 grams.

Sufficient soft ice mixture was placed in a bag made of flexible non-porous material to provide a package about 1 cm thick. The composition was frozen at about −5° C. over night. The package containing the "ice" was removed from the freezer and wrapped around a test tube containing a biological sample.

Particularly preferred packaging allows maximum flexibility whilst providing protection for the material being cooled using the pack. A preferred packaging material consists of a water-proof inner layer covered with a porous layer. The inner and outer layer of the packaging may be laminated to each other. Packs of the invention may be equipped with extensions such as tabs and ties for use in holding the packs against the material to be cooled. Extensions may have fastening means such as hooks and eyes, VELCRO™ or straps and buckles to provide means for holding the packs in place. Packs of the invention are useful for medical treatment to stop bleeding, relieve pain and constrict blood vessels. If the packs become too hardened for the particular use, they may be softened by kneading with the hands.

The packs of the invention will allow a researcher to retain an easily degraded sample on the laboratory table top for several hours after the sample has been removed from the freezer. Packs of the invention are particularly useful for storage of vaccines in the clinical setting when large numbers of individuals are to be treated at one time.

The packs of the invention are also useful for shipping short distances when refrigerated carriers are not available for use. For example, when animals are shipped short distances, packs containing soft ice may be placed over a grid support in the compartments to keep the animals cool. It is also possible to place fans under the supports to circulate the air. In fact, one of the problems that may arise when laboratory animals are shipped in air-conditioned compartments is that the refrigeration unites may contain infectious organisms if those units are not properly cleaned. The use of soft ice packs which can be refrozen in conjunction with more easily cleaned fans may prevent infection of the animals.

In many parts of the world, there are few if any, carriers with air conditioned compartments. Under such circumstances, the compartments may be divided to provide an area for very large packages containing soft ice. After use, the soft ice packs may be refrozen for reuse.

Relatively small packs of the invention may be used placed in smaller containers for transportation of heat-sensitive materials.

Figure 2:
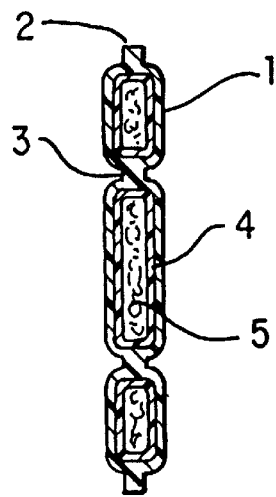
FIG. 2 shows a cross-section of a pack of the invention.

Referring to FIG. 1, the packaging may be in the form of a cushion. Referring to FIG. 2, the packaging consists of a porous outer layer (1), and an inner non-porous layer (4). The porous layer forms an edge (2) and the porous layer forms a space (5) for holding the colloidal "soft ice". The packaging may contain areas lacking in the colloidal filling material (3). Such areas further stabilize and strengthen the over-all pad. The outer porous layer provides strength to the packaging and causes the packs to be more comfortable to the touch. The areas lacking colloidal filling material also cause the total package to be more flexible.

Figure 3:
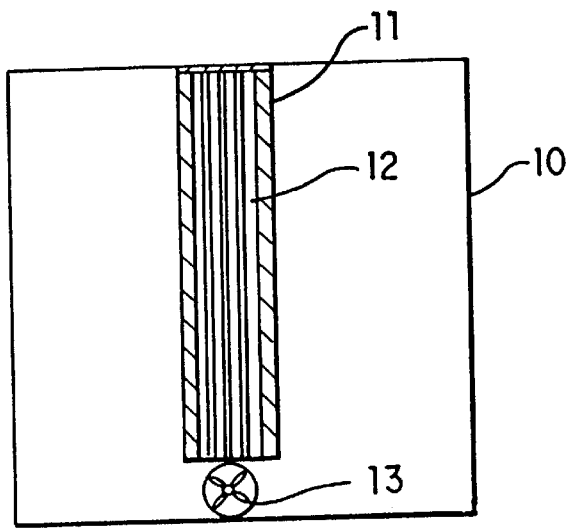
FIG. 3 shows a shipping container with compartments for holding packages of soft ice.
Figure 4:
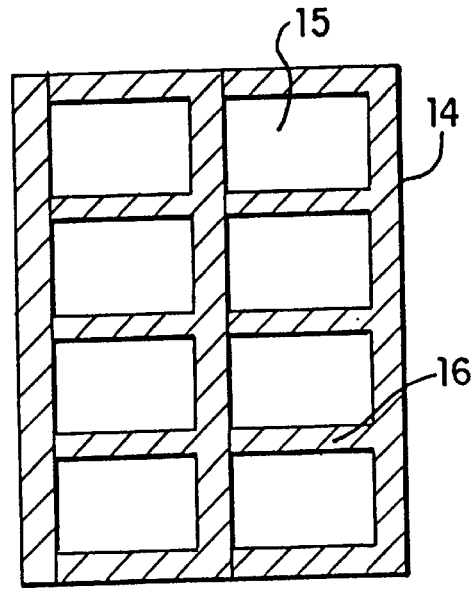
FIG. 4 shows a view of the supporting grid.

Referring to FIG. 3, the container (10) may be divided by support means (11) to hold packages of soft ice (12). Fans (13) are placed in the compartment to provide circulation. FIG. 4 a view of the support grids (14) having openings (15) in the supporting grid. The grids may have horizontal supports (16) which will divide the space in the grids so that smaller packages of soft ice may be used.

For providing cooling to animals, the support grids may be placed on the floor or sides of the compartment. The amount of cooling can be partially controlled by the amount of circulation in the compartment. While the cooling methods of the invention may be particularly useful for shipment of laboratory animals, the cooling means may also be quite useful for shipping animals to be butchered. Animals, especially poultry, can become ill and die during shipment. Breeding animals who become infected are much more likely to become ill and introduce infections into the flock or herd if subjected to heated conditions during transport. Resulting infections may result in spread of diseases to man.

EXAMPLE 2

A composition is prepared in accord with the method and sequence of Example 1 with lesser amounts of glycerine and polyacrylamide. To 500 grams of water is added 40 grams sodium sulfate with mixing until the sulfate had been dissolved. 90 grams glycerine and 20 grams polyacrylamide are then added to the water/salt solution and the whole is mixed until a colloidal composition was obtained, after which water is added to provide a total weight of 1000 grams.

EXAMPLE 3

A composition is made in accord with the teachings of Example 1 using, in place of sodium sulfate, sodium chloride.

While other chlorides and sulfates such as zinc chloride, potassium chloride and potassium sulfate may be used in accord with the teachings of this disclosure, the sodium chloride and sodium sulfate are effective and less costly than other salts.

The packaging may be in any shape, including shapes described in the cited U.S. Patents incorporated herein by reference. When the package consists of an inner non-porous layer and an outer porous layer, the two layers may be laminated together. In a preferred embodiment, the outer layer is larger than the inner layer and extends beyond the inner layer.

The packaging may contain areas which contain none of the soft ice filling. Materials which impart stability to the final pack may be used in all or part of the packaging.

EXAMPLE 4

An inner, non-porous bag of polyethylene having dimensions of 40 cm by 40 cm is prepared having an opening in one of four side edges and three edges of the bag forming the sides and bottom thermally sealed. The open edge forming the top is partially sealed by application of heat. The colloidal material prepared in Example 1 that has been allowed to sit for 1 hour since preparation is poured into the unsealed opening into the bag to fill the bag ½ full. Excess air is forced from the bag and the opening is sealed thermally.

A bag 45 cm wide and 45 cm long of tightly woven nylon is prepared having an opening in one of four side edges. A seam is sewn on three edges of the bag forming the sides and bottom. A second seam is sewn around the sides and bottom of the bag 2.5 cm from the previously sewn seam at the edge of the bag. The polyethylene bag containing soft ice composition is placed into the nylon bag. The edges of the open top of the bag are turned inside and the top of the bag is sewed closed. A second seam is sewed inside the first seam at the top of the outer bag.

The use of the double layer for the packaging provides a strong outer layer that helps protect the bag of non-porous material. It is also possible to fuse the two layers by heat or to laminate the layers together. In that instance, the bag of laminated material may be prepared in accord with the instructions for the preparation of the inner layer. The opening may then be thermally sealed. The fabric covering is more comfortable against the skin and is less prone to adhere to certain kinds of material such as super-cooled metal.

When the pack is to be used for medical treatment, or if flexibility is required for some other reason, such as when containers are to be wrapped in the packs, the pack will be more flexible if the packaging is not too full. Some of the packs described below are particularly useful when flexibility is required for wrapping around containers or body parts.

EXAMPLE 5

An elongated pack may be made which can be shaped to fit various parts of the body. Before filling, the pack comprises a water-proof envelope having a first and second side and, further, having an open end and a closed end, said open end being sealable. The pack may, additionally, be equipped with straps or other fastening means to hold said pack in place. Such means may be, for example, straps with buckling means. The water-proof envelope may be made of materials such as rubber or fabric laminated to polymeric materials such as polyethylene. After filling with soft ice in the manner described in Example 4, the open end is sealed by any suitable means such as a clasp, a sealing strip or by heat. The pack may then be frozen and used, then refrozen for reuse repeatedly.

Figure 5:
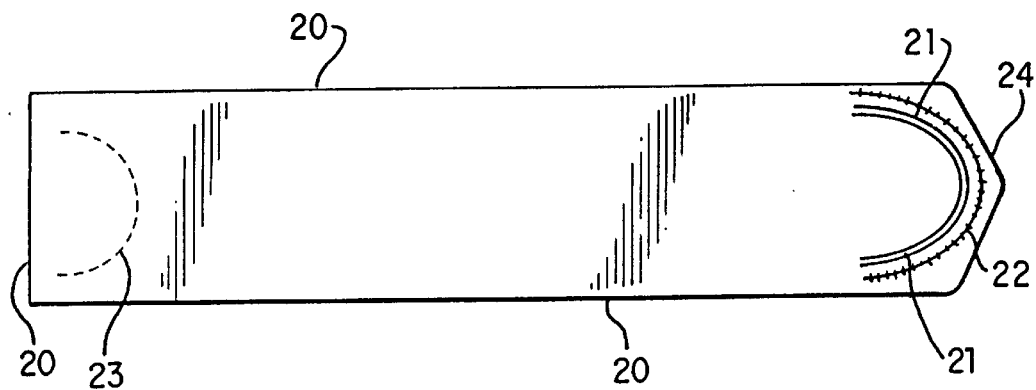
FIG. 5 shows an elongated pack.

The ends of the pack may be brought together or into close proximity to each other by means of straps which may have buckling means or loop-like material engageable with a fastening tab. Referring to FIG. 5, the elongated pack having closed edges (20), an open end (24) with sealing strips for closing (21) after the soft ice has been poured into the package, a strip of loop-like material on the first side (22) and a strip of material for accepting loops of loop-like material on the second side (23).

EXAMPLE 6

Figure 6:
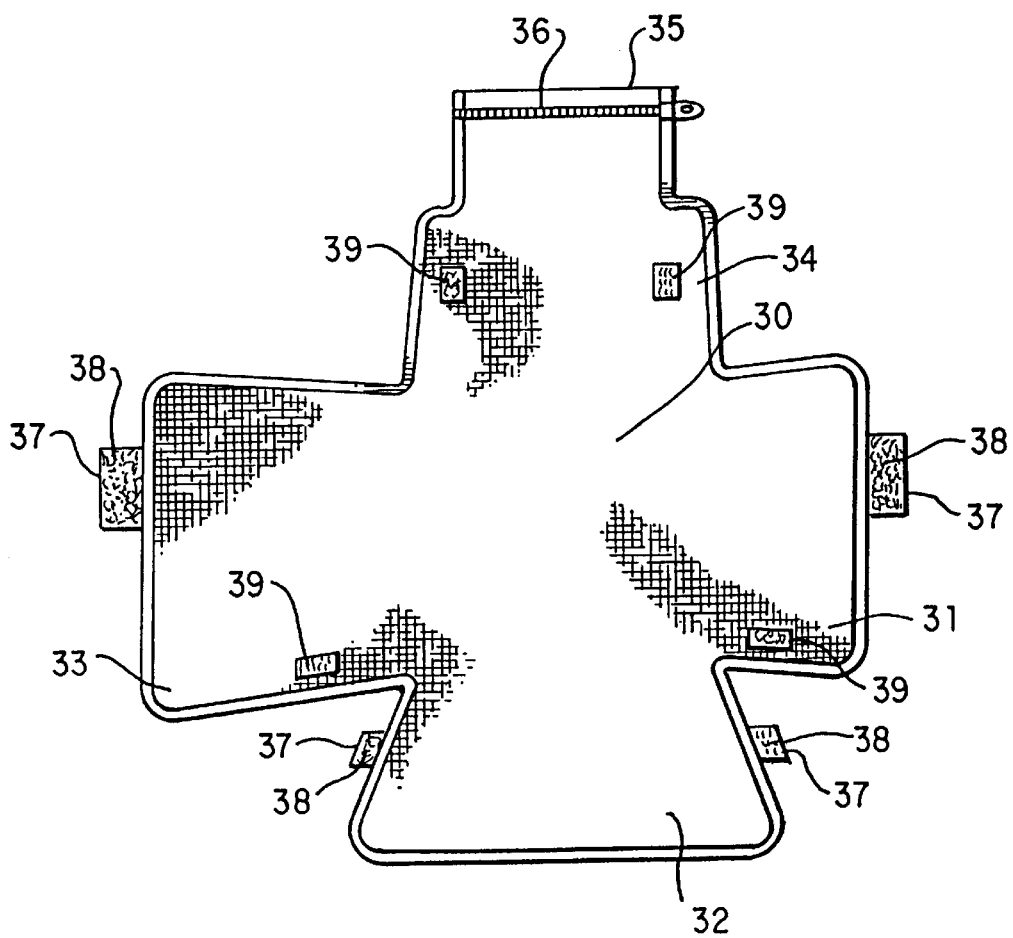
FIG. 6 shows a pack having 4 extensions.

A pack which may be contoured to conform to a body contour such as the chin or a joint is useful. Such a pack is shown in FIG. 6. Said pack has a central portion (30) and four radially extending portions (31, 32, 33, and 34). The relative arrangements of the central body portion and the four radially extending portions forms a cross-shaped ice pack. One of the radially extending members has an opening (35) at the end to allow the introduction of soft ice. The opening is opened and resealed with suitable closure means (36) such as the device shown in U.S. Pat. No. 4,532,353 by Hubbard, which is incorporated herein by reference in its entirety, or a water-tight zipper arrangement. The pack is filled in accord with the teachings of Example 4, with care taken to assure that all of the extending portions are about half filed. If the pack is relatively flat during cooling, it is easier to work with. However, should the soft ice become overly cold and hard, the pack may be kneaded with the hands to make the pack more pliable. The pack may be held in place with straps with fastening means. Strips (37) with VELCRO™ or similar loop-like materials (38) may be secured at sites (39) having means for accepting loops of loop-like materials.

The instantly claimed invention provides a material that retains lower temperatures than the compositions wherein the glycerine and polyacrylamide are present to a lesser degree without adding greatly to the expense involved in preparation. The more useful solution of the inventon requires that at least 15% of the composition by weight be glycerine plus polyacrylamide, with glycerine being present at at least 12% and polyacrylamide being present at a rate of at least 3%.

What is claimed is:

1. A composition of matter comprising 70% to 80% water, 5–10% salt, 12–15% glycerine and 3–5% polyacrylamide.

2. A composition of claim 1 wherein the salt is sodium chloride.

3. A composition of claim 1 wherein the salt is sodium sulfate.

4. A shipping compartment containing:
   1. support means for holding packages and
   2. packages containing a colloidal composition of claim 1.

5. A shipping compartment of claim 4 containing, additionally, air circulation means.

6. A shipping compartment of claim 4 wherein the support means are arranged in a vertical fashion and have, additionally, more than one horizontal support.

7. A shipping compartment of claim 5 wherein the support means are arranged in a vertical fashion and have, additionally, more than one horizontal support.

8. A method of producing soft ice containing 70% to 80% water, 5–10% salt, 12–15% glycerine and 3–5% polyacrylamide comprising the steps of:
   1) dissolving salts in water,
   2) adding to the product obtained in step 1 the glycerine and polyacrylamide, with or followed by mixing, and
   3) freezing the product obtained in step 2.

9. A method of claim 8 wherein, after step 2, the composition obtained at the end of step 2 is poured into a pack before freezing.

10. A method of preparing a colloidal composition containing 70% to 80% water, 5–10% salt, 12–15% glycerine and 3–5% polyacrylamide, wherein the salt is chloride and/or sulfate comprising the steps of:
   1) dissolving the chloride or sulfate salt in water,
   2) adding glycerine and polyacrylamide to the product obtained in step 1, and
   3) mixing the product obtained in step 2 until a colloidal suspension is formed.

* * * * *